United States Patent [19]

Hsieh et al.

[11] Patent Number: 5,481,115

[45] Date of Patent: Jan. 2, 1996

[54] ELECTRONIC CALIBRATION OF SINGLE PHOTON EMISSION COMPUTED TOMOGRAPHY CAMERAS

[75] Inventors: Yu-Lung Hsieh; Gengsheng L. Zeng; Grant T. Gullberg, all of Salt Lake City, Utah

[73] Assignee: University of Utah, The, Salt Lake City, Utah

[21] Appl. No.: 170,811

[22] Filed: Dec. 20, 1993

Related U.S. Application Data

[63] Continuation-in-part of Ser. No. 27,882, Mar. 8, 1993, Pat. No. 5,338,936, which is a continuation-in-part of Ser. No. 712,676, Jun. 10, 1991, Pat. No. 5,210,421.

[51] Int. Cl.$^6$ .............................. G01T 1/166; G01T 1/20
[52] U.S. Cl. .................. 250/363.04; 250/252.1; 250/363.07; 250/363.09
[58] Field of Search .................. 250/363.09, 363.07, 250/363.04, 252.1 R

[56] References Cited

U.S. PATENT DOCUMENTS

| 4,527,057 | 7/1985 | Guyton et al. | 250/252.1 R |
|---|---|---|---|
| 4,633,398 | 12/1986 | Gullberg et al. | 364/413.21 |
| 4,696,624 | 9/1987 | Ichihara | 250/363.04 |
| 4,703,424 | 10/1987 | Gullberg et al. | 364/413.21 |
| 4,812,983 | 3/1989 | Gullberg et al. | 364/413.17 |
| 5,173,608 | 12/1992 | Motomura et al. | 250/363.09 |
| 5,210,421 | 5/1993 | Gullberg et al. | 250/363.04 |

FOREIGN PATENT DOCUMENTS

| 57-69269 | 4/1982 | Japan | 250/363.07 |
|---|---|---|---|
| WO91/00048 | 1/1991 | WIPO . | |

OTHER PUBLICATIONS

"Review of Convergent Beam Tomography in Single Photon Emission Computed Tomography", Gullberg, et al., Phys. Med. Biol. 1992, vol. 37, No. 3, pp. 507–534.
"Automated Body Contour Detection in SPECT: Effects on Quantitative Studies", Hosoba, et al., J. Nucl. Med. 27:1184–1191, 1986.
"Estimation of Geometrical Parameters For Fan Beam Tomography", Gullberg, et al., Phys. Med. Biol., vol. 32, No. 12, 1581–1594 (1987).
"Estimation of Geometrical Parameters and Collimator Evaluation For Cone Beam Tomography", Gullberg, et al., Med. Phys. 17 (2) Mar./Apr. 1990 pp. 264–272.
"Reconstruction Algorithm For Fan Beam With a Displaced Center–of–Rotation", Gullberg, et al., IEEE Trans. Med. Imag., vol. MI–5, No. 1, Mar. 1986 pp. 23–29.
"Contributions to Cone Beam Tomography", Fuhrmann, et al.

*Primary Examiner*—Constantine Hannaher
*Attorney, Agent, or Firm*—Fay, Sharpe, Beall, Fagan, Minnich & McKee

[57] ABSTRACT

A SPECT camera (A) includes a plurality of detector heads (12a, 12b, 12c) which rotate around an examination region (10). A reconstruction processor (50) reconstructs output projection data from the detector heads into a three-dimensional image representation which is stored in an image memory (62). Selected data from the image memory (62) is converted to a human-readable display on a video monitor (66). To adjust automatically for detector head misalignment, a calibration phantom (B) which has two orthogonal lines of scintillators ($20_1$, $20_2$, $20_3$, $20_4$, $20_5$) arranged orthogonal to each other with a common scintillator in both lines is positioned in the examination region. As the detector heads rotate around the phantom, a misalignment parameter generator (40) generates the displacement distance of the actual rotation from the theoretical rotation axis ($\tau$), the actual rotation radius (R), a projection of the location of the focal point on a detector plane of the detector head in the transaxial direction ($C_\xi$), and a focal length of the collimator (F). A correction processor (42) corrects the reconstruction processor (50) in accordance with the generated misalignment parameters. In the preferred embodiment, the correction processor provides a revised weighting function to the reconstruction processor and modifies its backprojection algorithm.

18 Claims, 7 Drawing Sheets

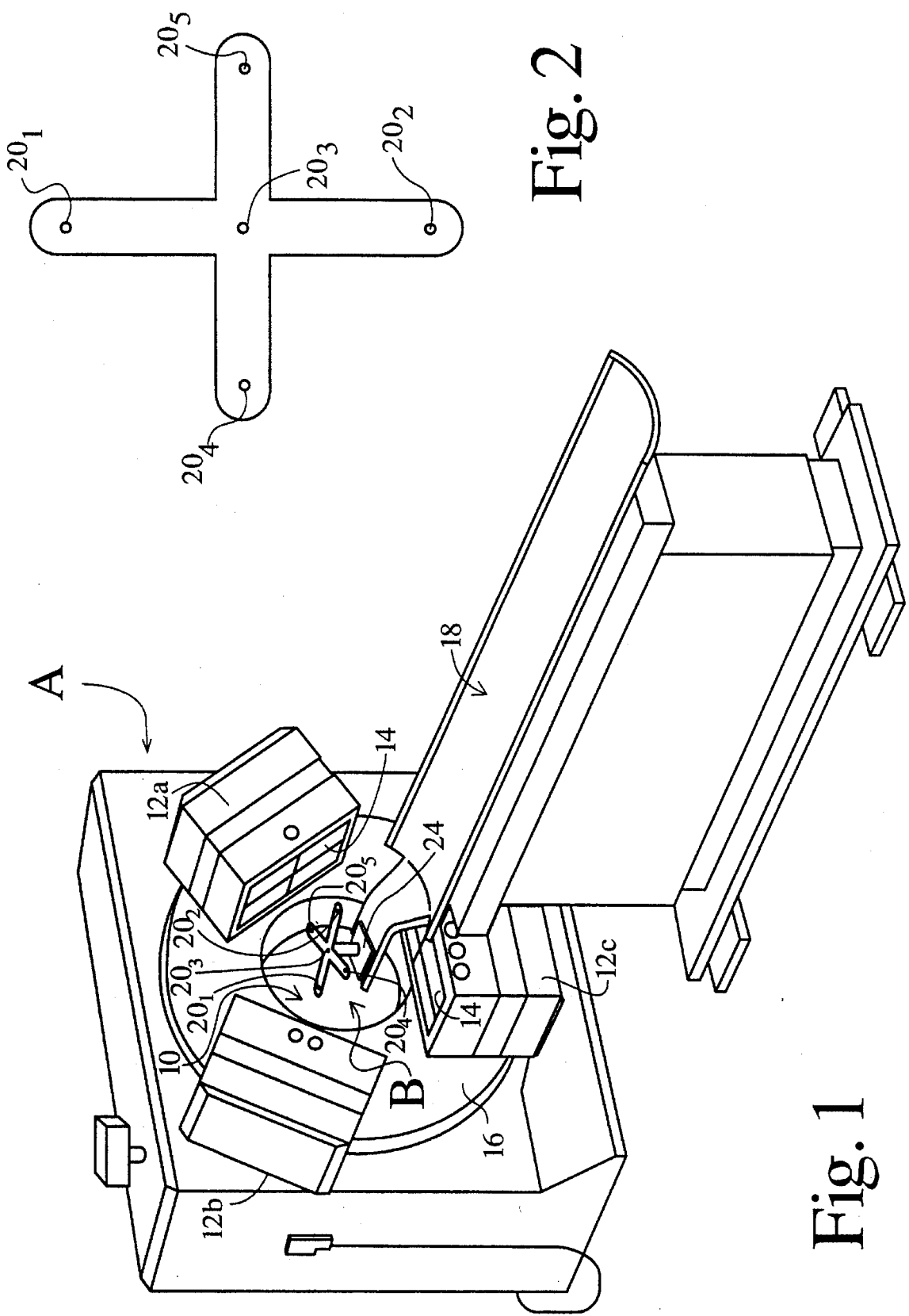

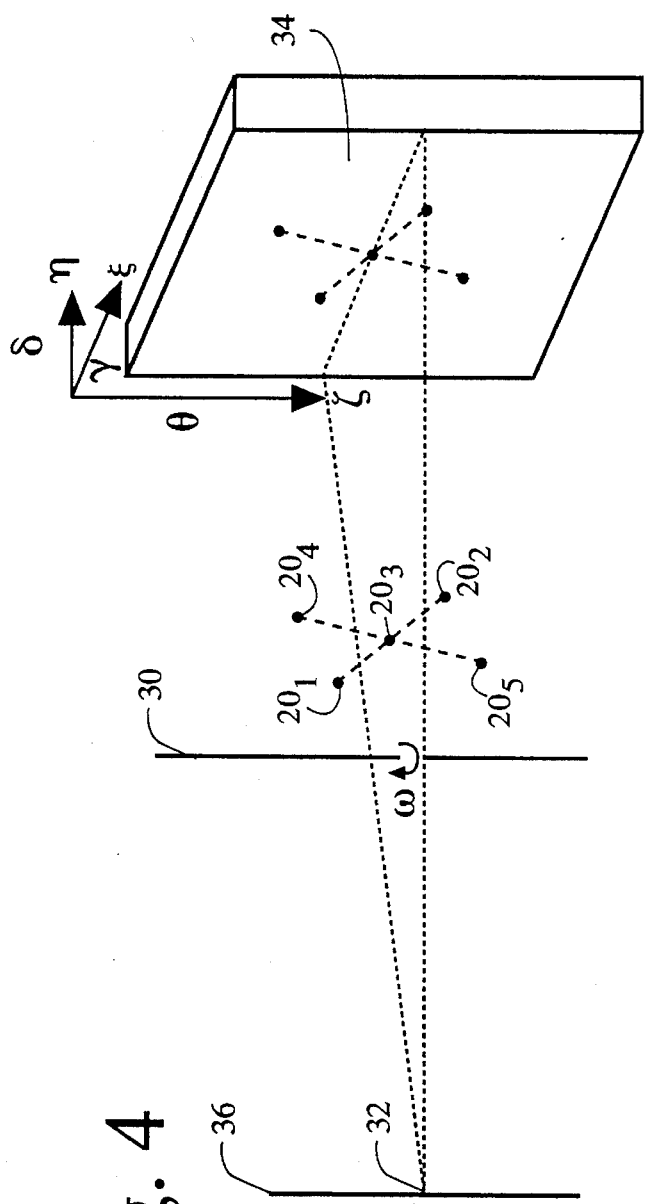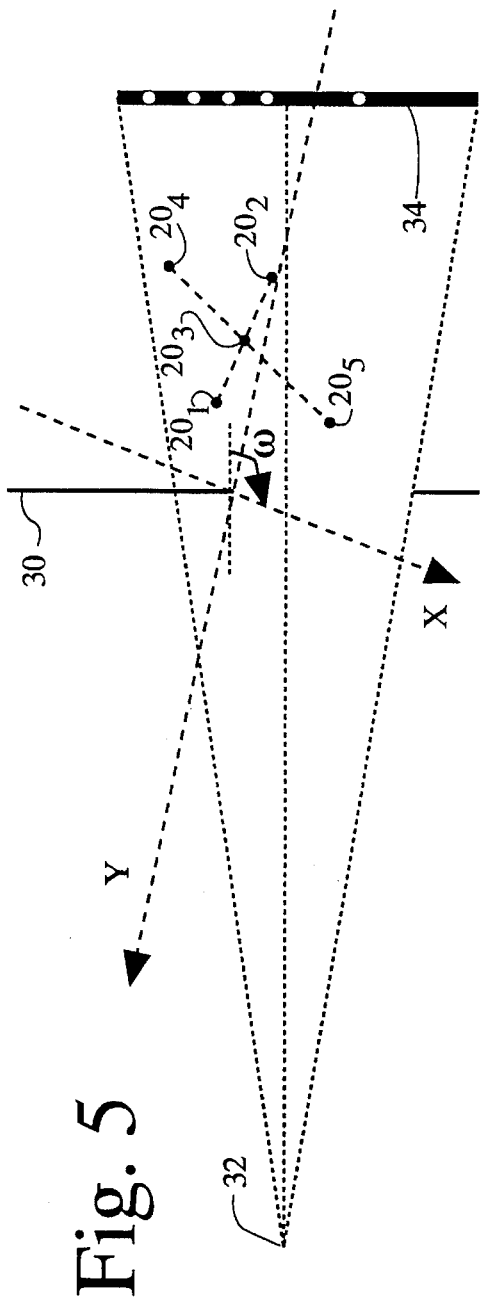
Fig. 4
Fig. 5

ELECTRONIC CALIBRATION OF SINGLE PHOTON EMISSION COMPUTED TOMOGRAPHY CAMERAS

The present application is a continuation-in-part of U.S. application Ser. No. 08/027,882 filed Mar. 8, 1993, now U.S. Pat. No. 5,338,936, which, in turn, is a continuation-in-part of U.S. application Ser. No. 07/712,676 filed Jun. 10, 1991, now U.S. Pat. No. 5,210,421.

BACKGROUND OF THE INVENTION

The present invention relates to nuclear cameras, also known as scintillation cameras, gamma cameras, or Anger cameras. The invention finds particular application in conjunction with multiple rotating head cameras, particularly SPECT cameras and will be described with particular reference thereto.

SPECT cameras commonly include a plurality of detector heads, e.g. three heads, which are mounted for rotation about a subject receiving examination volume. Typically, the heads can be moved closer together or further apart to accommodate different size subjects and different types of examinations.

Each of the heads includes a plate of scintillation material having a radiation receiving surface of about 30–50 cm ×60–90 cm. The scintillation material, typically a relatively thick crystal, is mounted closely adjacent a plurality of photomultiplier tubes. Each time a radiation event occurs within a subject, it sends out radiation which strikes the scintillation crystal causing a scintillation or flash of light. The electronic circuitry connected with the full photomultiplier tubes analyzes the output of the photomultiplier tubes and provides an indication of the coordinates on the scintillation crystal face at which each scintillation occurs. From the location on the scintillation crystal at which each scintillation is detected, and the angular position of the detector head around the subject, a three-dimensional map of radiation sources in the subject is conventionally derived.

In order to coordinate the location of a scintillation event with a region of the subject, the radiation must travel to the scintillation crystal along a predictable trajectory. To this end, collimators are mounted to the detector heads to control the trajectories along which radiation must travel in order to reach the scintillation crystals. The collimators are traditionally a grid of lead vanes that are mounted on the face of the scintillation crystal. Typically, a plurality of interchangeable collimators are provided for different studies. The collimators can have vanes of different lengths, grids with different densities of vanes, vanes which define trajectories perpendicular to the scintillation crystal face, vanes which define trajectories along a cone having a common apex or origin, trajectories along cones with pieces different distances from the detector head, trajectories along divergent fans which magnify in only one direction, or the like. The collimators, which typically weight several hundred kilograms, have a wide variety of substantial weights. Moreover, the detector heads themselves contain significant amounts of lead to shield the components from stray radiation.

The large interchangeable masses of the collimator and the detector heads, the rotation of the heads, the radial adjustment of the heads, and other mechanical operations place tremendous strains on the mechanical support structures. These and other factors can cause the heads to become misaligned. It is to be appreciated, that the reconstruction of the physical positions of the radiation sources assumes that radiation is being received by the detector heads along preprescribed trajectories. Any error in the actual trajectory along which radiation is received will cause a loss of resolution and other defects in the resultant reconstructed image. Any mechanical misalignment of the detector head due to camming, tipping, errors in radial positioning or the like, cause the actual trajectory to differ from the trajectories prescribed by the reconstruction algorithm.

More specifically, small errors in the alignment of the actual and mathematical trajectories tended to cause blurring and enlargement of the apparent location of radiation sources. Greater misalignment could cause the apparent location of each radiation source to diverge into a ring of most probable locations. Further misalignment could cause still further errors, uncertainty, and loss of resolution in the resultant image, as well as artifacts which could lead to erroneous medical diagnoses.

Heretofore, checking the alignment and positioning of the detector heads was a time consuming and tedious operation. Once any mechanical misalignment was measured, manual adjustment by the technician or a repair engineer was needed to optimize the alignment.

The present invention contemplates a new and improved automatic calibration procedure which enables the reconstruction algorithm to be recalibrated automatically after conducting a single scan procedure.

SUMMARY OF THE INVENTION

In accordance with one aspect of the present invention, a nuclear camera system includes at least one radiation detector head with an attached collimator. A means is provided for moving the detector head relative to the examination region. An image reconstruction means reconstructs image data from the detector head into a diagnostic image representation which is stored in an image memory. At least portions of the image representation are selectively displayable on a display means. A calibration phantom which includes a plurality of radiation sources is removably insertable into an examination region of the nuclear camera. A means is provided for analyzing the data from the detector head as the detector head is moved relative to the phantom to generate detector head misalignment parameter values. An electronic correcting means corrects or adjusts the image reconstruction means in accordance with the misalignment parameter values.

In accordance with one more limited aspect of the present invention, the collimator is a convergent ray collimator.

In accordance with another more limited aspect of the present invention, the radiation sources of the phantom are arranged along two straight lines which have a fixed orientation relative to each other, preferably perpendicular.

In accordance with another more limited aspect of the present invention, the reconstruction means includes a weighting function means for weighting detector head data with a weighting function, a filtering means for filtering the weighted data, and a backprojector means for backprojecting the filtered, weighted data with a backprojection algorithm into the image representation. The correcting means includes means for adjusting the weighting function and the backprojection algorithm.

In accordance with another aspect of the present invention, a method of automatically recalibrating a nuclear camera is provided. The nuclear camera includes at least one radiation detector head, a convergent ray collimator focused at a focal line attached to the detector head, a means for rotating the detector head around the examination region, and an image reconstruction means for reconstructing image data from the detector head into a diagnostic image representation. A phantom is positioned in the examination region and the detector head rotated therearound. From the output data of the detector head generated while rotating around the phantom, values indicative of misalignment of the detector head are generated. The reconstruction means is automatically adjusted in accordance with the misalignment values.

One advantage of the present invention is that it is automatic. It is carried out without a maintenance engineer or other intervention by a trained technician. The potential for operator error is eliminated.

Another advantage of the present invention resides in its speed and simplicity. Recalibration can be performed with a single scan procedure. Recalibration is so simple that it can be performed whenever the collimators are changed, other head positioning adjustments are changed, even between patients, or the like.

Another advantage of the present invention is that the calibration phantom need not be positioned precisely. The initial value dependence problem of one, two, or three point calibration sources is eliminated, enabling calibration parameters to be accurately calculated and bin width to be estimated without assumption as to the location of the calibration phantom.

Still further advantages of the present invention will become apparent to those of ordinary skill in the art upon reading end understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 1 is a perspective view of a SPECT scanner in combination with a calibration phantom in accordance with the present invention;

FIG. 2 is a top, plan view of the calibration phantom;

FIG. 4 is a diagrammatic illustration illustrating projection of the calibration phantom onto a detector head;

FIG. 5 is a top or bird's eye view of the diagram of FIG. 4;

DETAILED DESCRIPTION OF THE PREFERRED EMBODIMENTS

Figure 3:
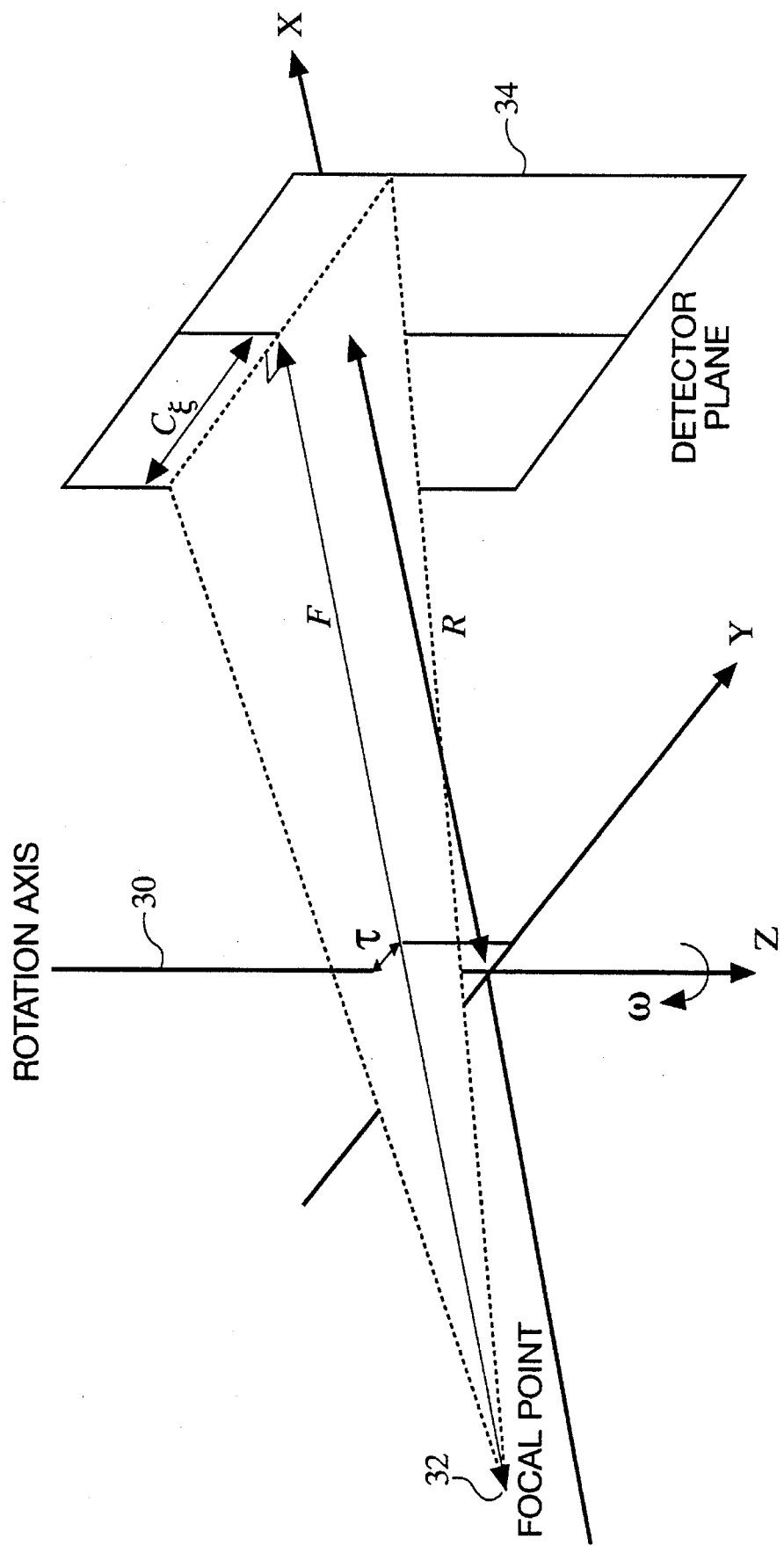
FIG. 3 is a diagrammatic view illustrating misalignment and calibration parameters.

With reference to FIG. 1, a SPECT camera system A has a calibration phantom B stably mounted temporarily in its examination region 10. The examination region is surrounded by three camera heads 12a, 12b, and 12c. As is conventional, each of the heads have a collimator 14 disposed toward the examination region in back of which lies a scintillation crystal and an array of photomultiplier tubes.

The heads are mounted on a rotatable member 16 which is mounted on bearings (not shown) and driven to rotate smoothly or in incremental steps by a motor (not shown). The motor is selectively actuated to rotate the rotatable member 16 and the detector heads 12a, 12b, and 12c circumferentially around the examination region. Preferably, the camera heads are mounted to be shifted by a radially, e.g. to be driven by a screw member to slide on radially disposed guides (not shown), for adjusting a radial displacement of the heads from a center of the examination region 10.

A patient support 18 is selectively adjustable in height and selectively insertable into and withdrawable from the examination region 10. This enables the head, torso, or other selected portion of a patient on the patient support 18 to be positioned in the examination region.

With continuing reference to FIG. 1 and further reference to FIG. 2, the phantom B includes a plurality of radiation emission sources $20_1$, $20_2$, $20_3$, $20_4$, and $20_5$, preferably point sources. The sources are arranged in a common plane and define two crossing lines and a point of intersection. More specifically, at least three point sources define each of the two intersecting lines. In the illustrated embodiment, point sources $20_1$, $20_3$, and $20_2$, define one straight line and $20_4$, $20_3$, and $20_5$ define the other straight line. Radiation source $20_3$ marks the point of intersection. For simplified mathematical processing, the two lines are orthogonal to each other and the radiation sources within each line are equidistant and linearly aligned.

The five radiation sources are mounted to a rigid former 22, such as a "+"-shaped piece of radiation transparent plastic. The plastic, in turn, is mounted to a base 24 which may again be of the radiation transparent plastic. The base is of an appropriate size and dimension to support the phantom B toward the center of the examination region.

With reference to FIG. 3, the rotatable gantry portion 16 and the detector heads 12 rotate about an axis of rotation 30. The collimator of the detector heads focuses the radiation trajectories along a series of fan-shaped paths with a focal point 32 which is a distance F from a detector plane 34, e.g. the scintillation crystal. The scintillation crystal is displaced from the axis of rotation by a rotation radius R. Ideally, the ray of the focal length F of the fan collimator which extends from the focal point 32 perpendicular to the detector face would intersect the axis of rotation and intersect the detector plane at its center. However, due to misadjustment or miscalibration, the central ray is often displaced from the axis of rotation 30 by a distance f. Moreover, the projection of the focal point 32 is centered at a distance $C_\xi$ in the transaxial direction. (Although ($\xi$) is illustrated as a fan-beam geometry for simplicity, the above-discussed also holds for cone-beam geometries). In a cone-beam geometry, there is a single focal point for all rays. For a fan-beam geometry, there is a focal line 36 which extends parallel to the axis of rotation and the detector head in the direction $\zeta$ (vertical in the embodiment of FIG. 3).

Figure 6:
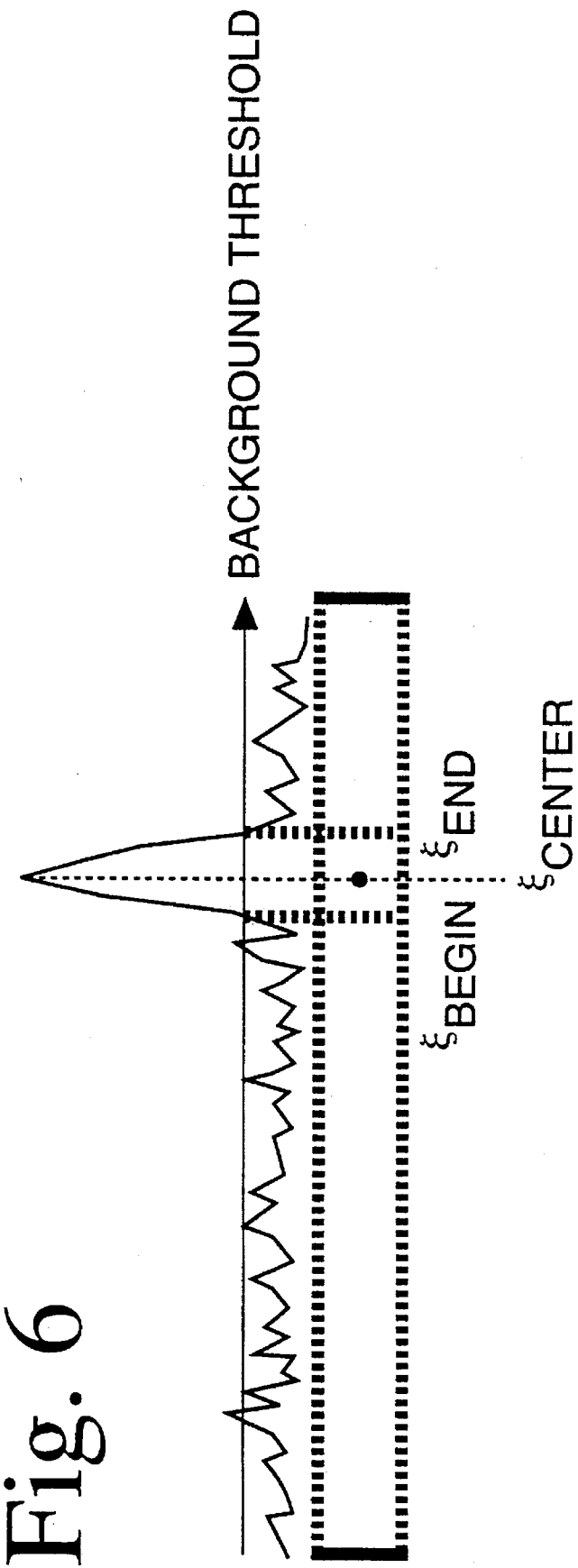
FIG. 6 illustrates a projection data profile in the transaxial ($\xi$) direction.
Figure 7:
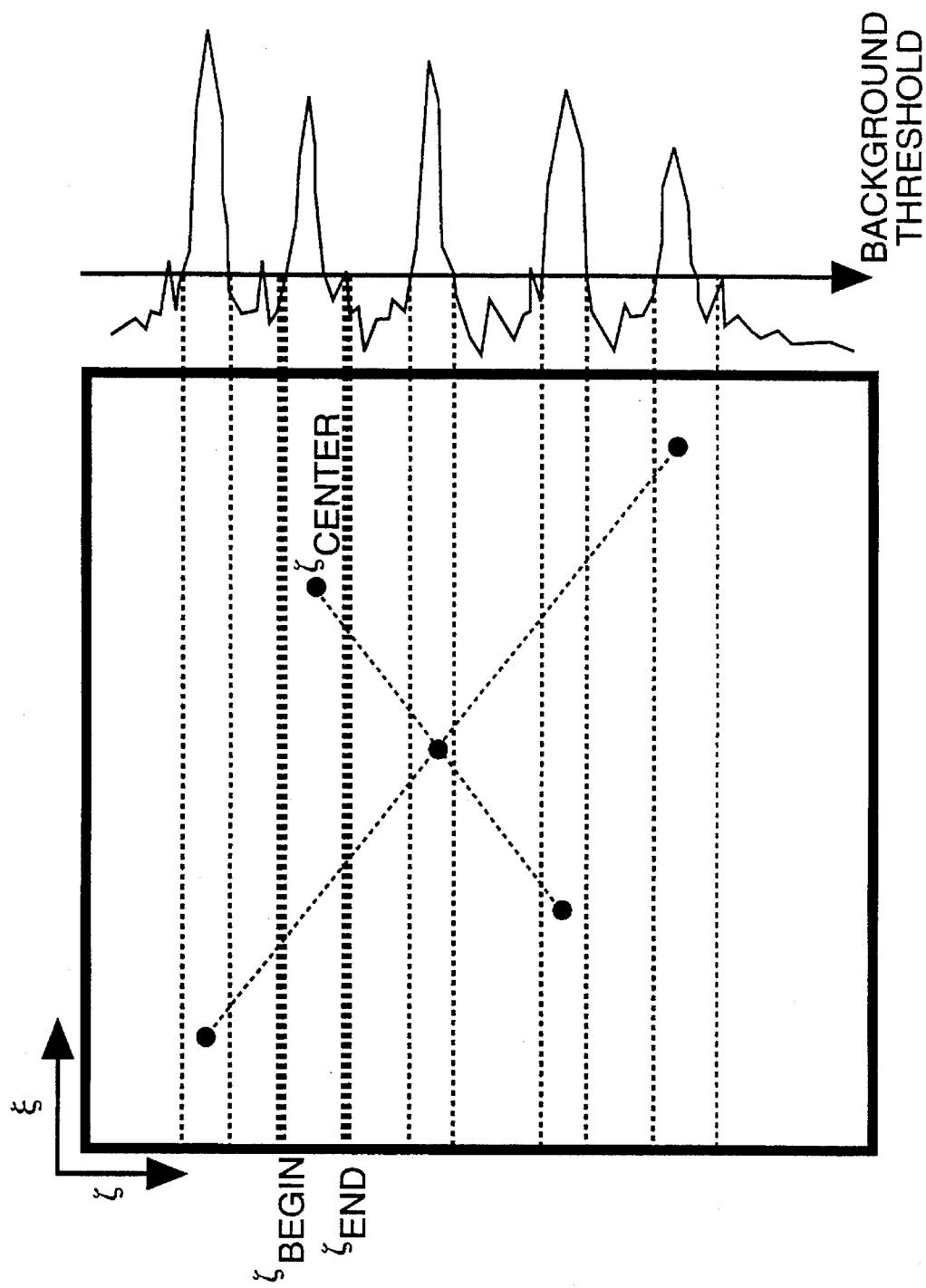
FIG. 7 illustrates two-dimensional projection data and a projected profile in the axial ($\zeta$) direction.

With reference to FIGS. 4 and 5, the phantom is positioned within the examination region such that no two point sources are in the same transverse slice and none are on the axis of rotation. Because the point sources are projected in different axial ($\zeta$) directions, the projection data can be thresholded and separated into five regions as in FIGS. 6 and 7. The projected location of each point source can be determined by calculating the center of mass for each region, i.e.

$$\zeta_{center} = \frac{\sum_{i=\zeta_{begin}}^{\zeta_{end}} \zeta_i \times value_i}{\sum_{i=\zeta_{begin}}^{\zeta_{end}} value_i} \quad (1)$$

$$\xi_{center} = \frac{\sum_{i=\xi_{begin}}^{\xi_{end}} \xi_i \times value_i}{\sum_{i=\xi_{begin}}^{\xi_{end}} value_i} \quad (2)$$

Figure 8:
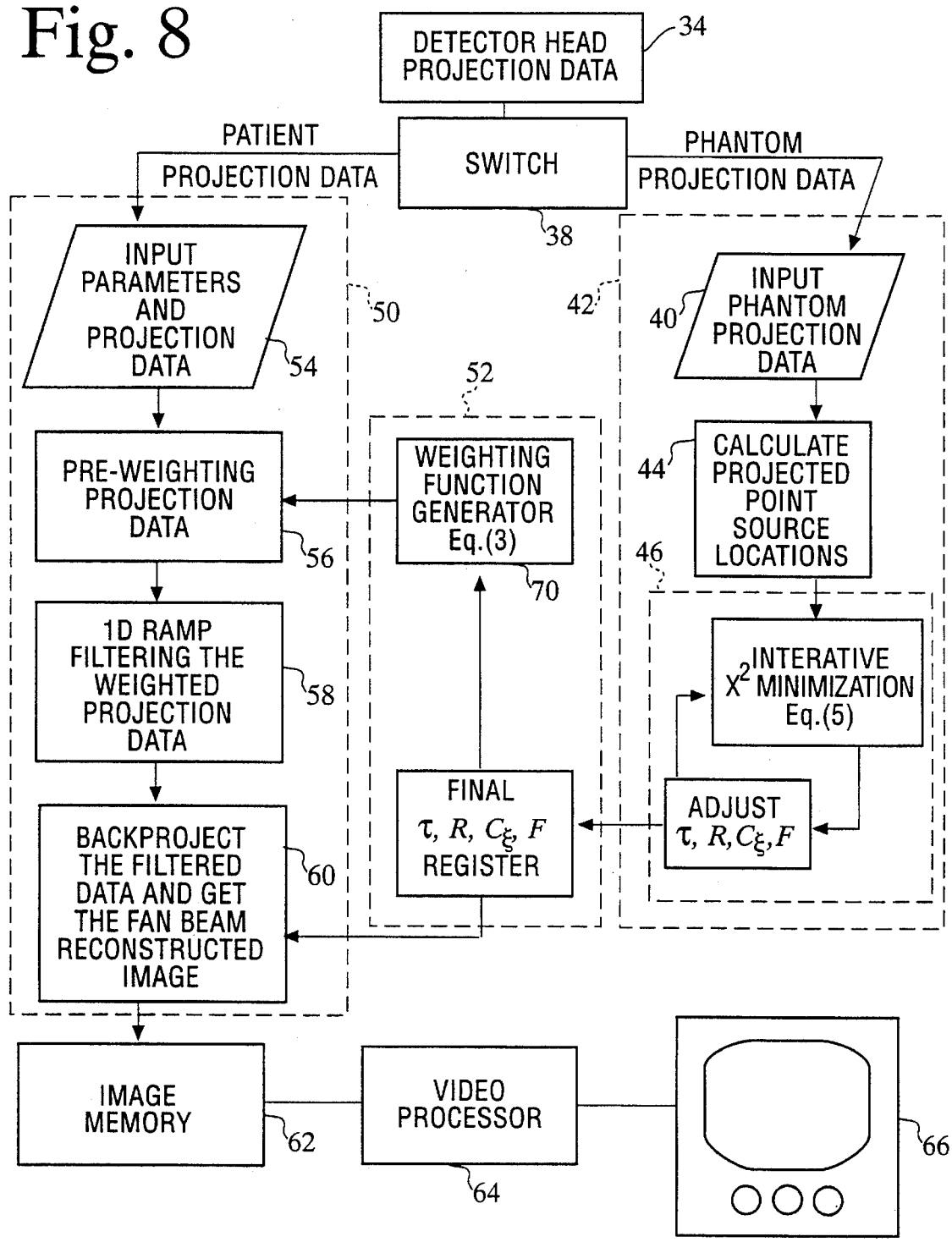
FIG. 8 is a diagrammatic illustration of image reconstruction and misalignment correction means in accordance with the present invention; and, FIG. 9 is a flow chart of Marquardt's algorithm, where a is a vector of calibration parameters and $\lambda$ is a factor for coordinating between the conjugate gradient algorithm and the steepest descent method.

With reference to FIG. 8, an input data means 40 of a correction means 42 which determines the geometric parameters and the coordinates of the point sources. A means 44 calculates the projected point source locations for each projected view.

Having determined the centroids of the projections of the five points, an iterative adjustment means 46 iteratively adjust the parameters $\tau$, R, $C_\xi$, and F, and the coordinates of the point sources to minimize the difference among the calculated and the measured centroids and optimize the linearity of each of the two three point lines and the orthogonality of the two lines.

After the correction means 42 has calculated the parameters $\tau$, R, $C_\xi$, and F, the switch 38 conveys patient projection data to a reconstruction means 50 which reconstructs the patient projection data into a three-dimensional image representation of an examined patient. A reconstruction algorithm adjustment means 52 adjusts the reconstruction algorithm of the reconstruction means for the corrected parameters $\tau$, R, $C_\xi$, and F. In particular, the reconstruction means 50 includes an input means 54 which receives the raw data q from the detector heads. A weighting means 56 weights the input projection data with a preliminary weighting function. A suitable weighting function W for fan-beam reconstructions is:

$$W = \frac{(F - \tau\xi/F)}{(F^2 + \xi^2)^{1/2}} \quad (3)$$

A filtering means 58 convolutes the weighted projection data by using a ramp filter. A backprojecting means 60 backprojects the filtered data to produce a three-dimensional imagine representation which is stored in a three-dimensional image memory 62.

A suitable backprojection algorithm 60 is to backproject each arbitrary filtered data q($\omega$,s') in the fan-beam plane to a point f(r,$\phi$) in the polar coordinate system:

$$f(r,\phi) = \int_0^{2\pi} q(\omega,s')/U^2 d\omega \quad (4)$$

where s'=[rFcos($\omega$-$\phi$)-$\tau$F]/[rsin($\omega$-$\phi$)+F]  U=[rsin($\omega$-$\phi$)+F]/F A video processor 64 selectively converts data in the image memory 62 into a human-readable display on a video terminal 66 or the like. The reconstruction adjusting means 52 includes a weighting function generator 70 which generates weighting functions W in accordance with the recalibration parameters, and merely changes the values of $\tau$, R, $C_\xi$, and F in the backprojection algorithm 60.

The iterative adjustment means 46 uses Marquardt's algorithm to minimize a combined $\chi$-square function to determine the $\tau$, R, $C_\xi$, and F parameters, and the coordinates of the point sources:

$$\chi^2 = \sum_{i=1}^{5} \chi_i^2(\tau,R,C_\xi,F;x_i,y_i) + \quad (5)$$

$$O^2(x_1,x_2,x_4,x_5;y_1,y_2,y_4,y_5;z_1,z_2,z_4,z_5) +$$

$$L_1^2(x_1,x_2,x_3;y_1,y_2,y_3;z_1,z_2,z_3) + L_2^2(x_3,x_4,x_5;y_3,y_4,y_5;z_3,z_4,z_5)$$

where $$O^2(x_1,x_2,x_4,x_5;y_1,y_2,y_4,y_5;z_1,z_2,z_4,z_5) = \quad (5a)$$
$$[(x_1 - x_2)(x_4 - x_5) + (y_1 - y_2)(y_4 - y_5) + (z_1 - z_2)(z_4 - z_5)]^2$$

$$L_1^2(x_1,x_2,x_3;y_1,y_2,y_3;z_1,z_2,z_3) = \quad (5b)$$
$$[(x_1 - x_2)(y_1 - y_3) - (x_1 - x_3)(y_1 - y_2)]^2 +$$
$$[(x_1 - x_2)(z_1 - z_3) - (x_1 - x_3)(z_1 - z_2)]^2 +$$
$$[(y_1 - y_2)(z_1 - z_3) - (y_1 - y_3)(z_1 - z_2)]^2$$

$$L_2^2(x_3,x_4,x_5;y_3,y_4,y_5;z_3,z_4,z_5) = \quad (5c)$$
$$[(x_5 - x_4)(y_5 - y_3) - (x_5 - x_3)(y_5 - y_4)]^2 +$$
$$[(x_5 - x_4)(z_5 - z_3) - (x_5 - x_3)(z_5 - z_4)]^2 +$$
$$[(y_5 - y_4)(z_5 - z_3) - (y_5 - y_3)(z_5 - z_4)]^2$$

where $O^2$ is the orthogonality of the two lines, $L_1^2$ is the linearity of one of the two lines, $L_2^2$ represents the linearity of the other line, and $x_i$, $Y_i$, $z_i$ are the positions of the point source i in the x, y, and z-directions, respectively. The Marquardt method varies smoothly between the extreme of the conjugate gradient method and the steepest descent method.

Briefly, the basic intention is to minimize the chi-squared difference between the measured centroid $\hat{\xi}_{mi}$ and the calculated centroid $\xi_{mi}$ in the transaxial ($\xi$) direction for a point source i at projection view m:

$$\chi_i^2 = \sum_{m_i} (\hat{\xi}_{m_i} - \xi_{m_i})^2 \times \sigma_{m_i}^{-2} \quad (6)$$

$$\xi_{mi}(\tau,R,C_\xi,F;x_i,y_i) = \frac{(x_i\sin\omega_m + y_i\cos\omega_m - \tau)F}{(x_i\cos\omega_m + y_i\sin\omega_m + F - R)} + C_\xi \quad (6a)$$

where $\omega_m$ is the rotation angle at the m-th projection view. To generalize this function, a new X-square function, which is a function of an estimation parameter vector a of M variables, is defined as:

$$\chi^2(a) = \sum_m [\hat{\xi}_m - \xi_m(\omega_m;a)]^2 \times \sigma_{\xi_m}^{-2} \quad (7)$$

where the model to be fitted is $\xi_m(\omega_m;a)$ for the projection data at the m-th projection view, and a is the Mx1 vector of parameters to be estimated. In the present application, the parameters a to be estimated are $\tau$, R, $C_\xi$, and F. Generally speaking, when the values are sufficiently close to the minimum, the function $\chi^2$ can be well approximated by a quadratic form of the Taylor series expansion:

$$\chi^2(a) = \chi^2(p) + \sum_m \frac{\partial \chi^2}{\partial a_m} \times a_m + \frac{1}{2} \times \sum_{m,n} \frac{\partial^2 \chi^2}{\partial a_m \partial a_n} \times a_m \times a_n + \ldots \quad (8)$$

$$\approx \gamma - d^T \times a + \frac{1}{2} a^T \times D \times a,$$

where p is a known value, d is an Mx1 vector of the first order derivatives, and D is an MxM matrix of second order derivatives. When the approximation is good, the current parameters $a^{(i)}$ to $a^{(i+1)}$, where the index i denotes the iteration number when the values are obtained, by the conjugate gradient formula:

$$a^{(i+1)} = a^{(i)} + D^{-1}[-\nabla\chi^2(a^{(i)})] \quad (9)$$

On the other hand, Equation (8) may be a poor local approximation to the shape of the function that is being minimized. In this case, the steepest decent method is used. A slow step is taken down the gradient of the concave surface instead of jumping to another local concavity. The steepest descent formula is given by:

$$a^{(i+1)} = a^{(i)} - \text{const} \cdot \nabla\chi^2(a^{(i)}) \quad (10)$$

The gradient of $X^2$ has the components:

$$\frac{\partial\chi^2}{\partial a_k} = -2\sum_m \frac{\hat{\xi}_m - \xi_m(\omega_m;a)}{\sigma_m^2} \frac{\partial}{\partial a_k} \xi_m(\omega_m;a) \quad (11)$$

$$k = 1, 2, \ldots, M$$

The partial derivative is:

$$\frac{\partial^2\chi^2}{\partial a_k \partial a_l} = 2\sum_m \frac{1}{\sigma_m^2}\left[\frac{\partial\xi_m(\omega_m;a)}{\partial a_k}\frac{\partial\xi_m(\omega_m;a)}{\partial a_l} - [\hat{\xi}_m - \xi_m(\omega_m;a)]\frac{\partial^2}{\partial a_k \partial a_l}\xi_m(\omega_m;a)\right] \quad (12)$$

$$\approx 2\sum_m \frac{1}{\sigma_m^2}\left[\frac{\partial\xi_m(\omega_m;a)}{\partial a_k}\frac{\partial\xi_m(\omega_m;a)}{\partial a_l}\right]$$

The second order derivative term can be dismissed when it is zero, or small enough to be negligible when compared with the term involving the first order derivative. Moreover, if the model fits badly or is contaminated by outlier points. The outlier points are unlikely to be offset by compensating opposite points. Therefore, the second order derivative term is sometimes unstable. In fact, ignoring the second order term generally has no affect at all on the final set of parameters a, but affects the iterative route which is taken to get there.

To describe how Marquardt's algorithm compromises the conjugate gradient and the steep descent algorithm to estimate the parameters, it is convenient to define three symbols:

$$\beta_k \equiv -\frac{1}{2}\frac{\partial\chi^2}{\partial a_k}, \quad (13a)$$

$$\alpha_{kl} \equiv \frac{1}{2}\frac{\partial^2\chi^2}{\partial a_k \partial a_l}, \quad (13b)$$

$$\delta a_k^{(i)} = a_k^{(i)} - a_k^{(i-1)}. \quad (13c)$$

where subindex k,l are the k-th and l-th variables of a, and superindex (i) indicates i-th iteration.

From Equation (10), at the i-th iteration, the steepest descent formula can be written as:

$$\delta a_k = \text{const} \cdot \beta_k \quad (14).$$

Because the quantity of $\chi^2$ is non-dimensional, $\beta_k$ has the dimensions of $1/a_k$ and $\delta a_k$ has the dimension of $a_k$. Marquardt noticed that the proportional constant between $\beta_k$ and $\delta a_k$ must have the dimension of $a_k^2$. Thus, he defined a factor $\lambda$ and correlated it to $\delta a_k$, $\alpha_{kk}$, and $\beta_k$:

$$\delta a_k = \frac{1}{\lambda\alpha_{kk}} \times \beta_k \quad (15)$$

From Equation (9), the conjugate gradient formula can be rewritten as a set of linear equations:

$$\sum_l \alpha_{kl}\delta a_l = \beta_k \quad (16)$$

Marquardt's second insight was that Equation (15) and Equation (16) can be combined as:

$$\sum_l \alpha'_{kl}\delta a_l = \beta_k \quad (17)$$

where $[\alpha']$ is a new positively defined matrix defined by:

$$\begin{cases} \alpha'_{kl} \equiv \alpha_{kl} \times (1+\lambda), & k = l \\ \alpha'_{kl} \equiv \alpha_{kl}, & k \neq l \end{cases} \quad (18)$$

When $\lambda$ is very large, the matrix $[\alpha']$ is forced into being diagonally dominated, and Equation (17) becomes identical to Equation (15). On the other hand, as $\lambda$ approaches zero, Equation (17) reduces to Equation (16).

Figure 9:
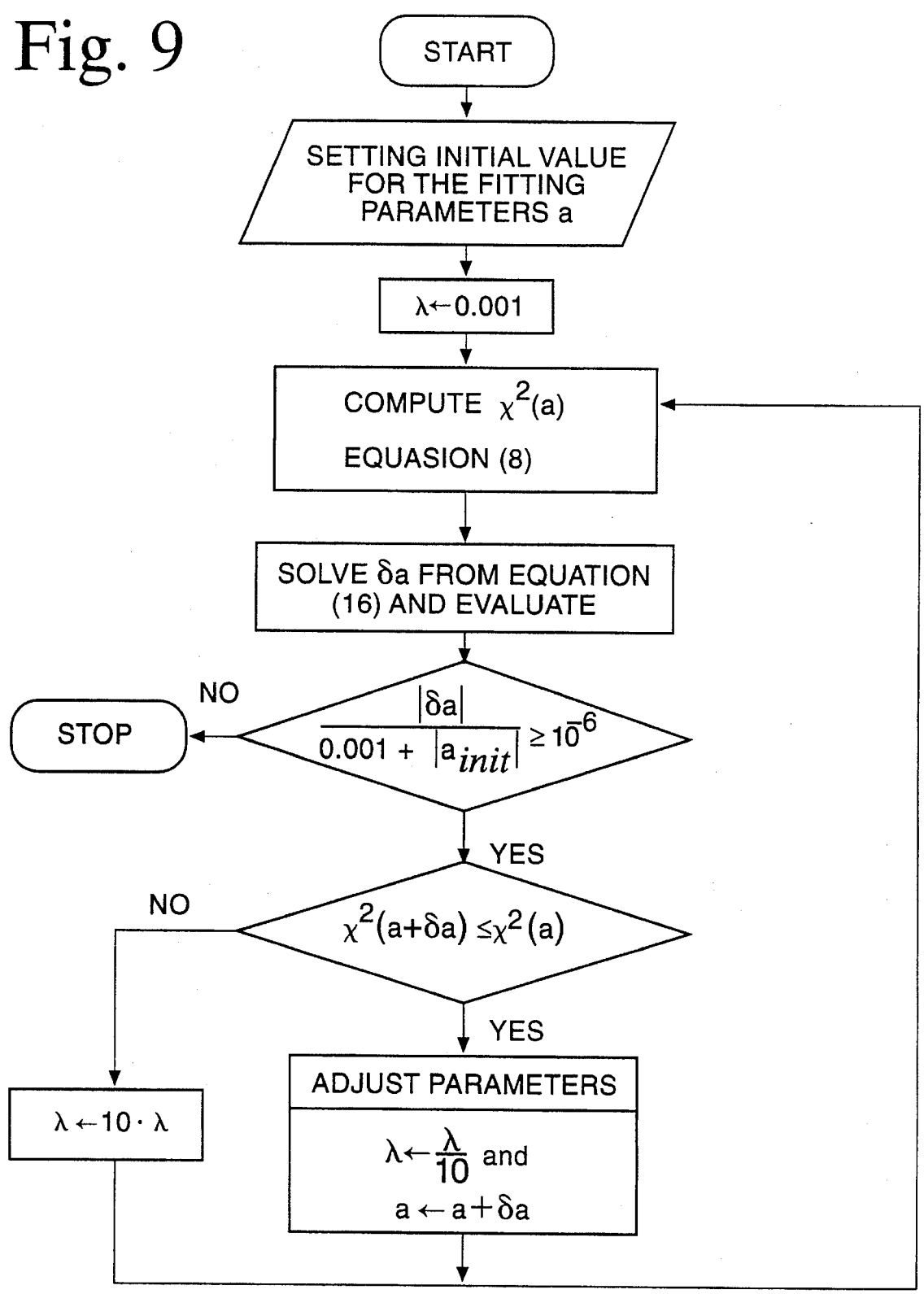

With reference to FIG. 9, a is a vector of fitting parameters and $\lambda$ is a factor for coordinating between the conjugate gradient algorithm and the steepest descent method. When the new $\chi^2$ value is larger than the old one, a larger step follows. Otherwise, a smaller step size is used. The gradient and step length are iteratively adjusted according to the calculated $\chi^2$ value to minimization. When the adjustment of all parameters are sufficiently small, by a preselected standard, the algorithm is assumed to be converged. All estimated parameters are at this point optimized.

Applying Marquardt's algorithm to the three point source calibration algorithm, the minimization can be done with respect to a line L along which three point radiation sources 1, 2, and 3 are disposed. Three $\chi^2$ functions, $\chi_1^2(\tau,R,C_\xi,F;x_1;y_1)$, $\chi_2^2(\tau,R,C_{86},F;x_2;y_2)$, and $\chi_3^2(\tau,R,C_\xi,F;x_3;Y_3)$, are minimized with the constraint $L^2(x_1, y_1, z_1; x_2, y_2, z_2; x_3, y_3, z_3)=0$ to estimate parameters $\tau$, R, $C_\xi$, F, $x_i$, $y_i$, and $z_i$. The parameters $\tau$, R, $C_\xi$, and F are common parameters in three $\chi^2$ functions. Group $x_i$, $y_i$ are parameters both in the constraint and in the $\chi_i^2$. Parameters $z_i$ are the fitting parameters only in the constraint.

An approach for a three point source calibration is to combine all the objective functions and the constraints as one $\chi^2$ function:

$$\chi^2 = \sum_{i=1}^{3} \chi_i^2(a;c_i) + L^2(c_1,c_2,c_3;d) \quad (19)$$

for $a=\tau$, R, $C_\xi$, and F; $c_i=x_i,y_i$; and $d=z_i$, $i=1,2,3$. The first order derivative functions are derived as:

$$\frac{\partial\chi^2}{\partial a} = \sum_{i=1}^{3} \frac{\partial}{\partial a}\chi_i^2(a;c_i), \quad (20)$$

$$\frac{\partial\chi^2}{\partial c_i} = \frac{\partial}{\partial c_i}\chi_i^2(a;c_i) + \frac{\partial}{\partial c_i}L^2(c_1,c_2,c_3;d), \; i=1,2,3 \quad (21)$$

$$\frac{\partial\chi^2}{\partial d} = \frac{\partial}{\partial d}L^2(c_1;c_2;c_3;d) \quad (22)$$

To use Marquardt's algorithm, a Hessian matrix $[\alpha]$ is provided:

$$\alpha_{kl} = \frac{1}{2}\frac{\partial^2\chi^2(\omega_m,a)}{\partial a_k \partial a_l} \quad (23)$$

where: $[\alpha]$ is a 10×10 matrix, $$1:[\alpha_{\chi_1^2}] = \left[ \frac{\partial^2 \chi_1^2}{\partial x \partial y} \right] \tag{24}$$

$$2:[\alpha_{\chi_2^2}] = \left[ \frac{\partial^2 \chi_2^2}{\partial x \partial y} \right] \tag{25}$$

$$3:[\alpha_{\chi_3^2}] = \left[ \frac{\partial^2 \chi_3^2}{\partial x \partial y} \right] \tag{26}$$

x, y, can be a, $c_k$, (k is the index of parameter c), $[\alpha_{xi}^2]$ is the Hessian matrix for the single $\chi^2$ function $\chi_i^2$.

$$L:[\alpha_L] = \left[ \frac{\partial^2 L^2}{\partial x \partial y} \right] \tag{27}$$

where x, y can be $c_k$, $d_l$ (k, l are the indices of parameters c and d). The estimated parameters approach the true value step by step. When the objective function is minimized, all of the sub-chi-square functions are also minimized.

This method can be expanded to optimize not only a single line, but the two orthogonal lines by minimizing the chi-squared function $\chi^2$ as defined in Equation (5) above. Because there are five radiation point sources, there are five $\chi^2$ functions $\chi_1^2(a;c_1)$, $\chi_2^2(a;c_2)$, $\chi_3^2(a;c_3)$, $\chi_4^2(a;c_4)$, and $\chi_5^2(a;c_5)$ with three constraints $L_1^2(c_1, c_2, c_3; d_1, d_2, d_3)$, $L_2^2(c_3, c_4, c_5; d_3, d_4, d_5)$, and $O^2(c_1, c_2, c_4, c_5; d_1, d_2, d_4, d_5)$ to estimate parameter sets a, c, and d, where a=τ, R, $C_{86}$, and F; $c_i=x_i, y_i$; and $d_i=z_i$.

The Hessian matrix $[\alpha]$ is formed from the second order derivative functions:

$$i:[\alpha_{\chi_i^2}] = \left[ \frac{\partial^2 \chi_i^2}{\partial x \partial y} \right], i=1,2,3,4,5 \tag{28}$$

where x, y can be a, $c_k$, (k is the index of parameters c).

$$L_i:[\alpha_{L_i}] = \left[ \frac{\partial^2 L_i^2}{\partial x \partial y} \right], i=1,2 \tag{29}$$

where x, y can be $c_k$, $d_l$, (k, l are the indices of parameters c and d)

$$O:[\alpha_O] = \left[ \frac{\partial^2 O^2}{\partial x \partial y} \right] \tag{30}$$

where x, y can be $(c_1, c_2, c_4, c_5)$, and $(d_1, d_2, d_4, d_5)$.

In this manner, when the combined $\chi^2$ function is minimized, all the optimal fitting parameters are produced. For parallel and fan-beam collimators, imperfectly stacked corrugated lead sheets can make the collimator have different focal lengths F and different rotational shift τ for different slices. However, for computational simplicity, the following discussion assumes that the detector plane is not tilted and that the fan-beam collimator geometry can be described by a single focal length F and one rotational displacement τ for all transverse slices. Because the detector is not tilted, from the geometry characteristics of the fan-beam collimator, $z'_1$, $z'_2$, and $z'_3$ can be assumed to be the same as $\xi_m$, the average projected point source location in the ζ-direction. For each point source in the m-th projection view, one needs only consider $\xi_m$, the projected location of the source in the ξ-direction on the detector plane. The geometric parameters that need to be calibrated are the displacement of the rotational axis τ, the focal length F, the rotational radius R, and the projected location of the focal point of the detector plane $C_{86}$. For three points sources $\chi^2$ is defined as:

$$\chi^2 = \chi_1^2 + \chi_2^2 + \chi_3^2 + L^2 \tag{31}$$
$$= \sum_{m_1} (\hat{\xi}_{m_1} - \xi_{m_1})^2 \times \sigma_{m_1}^{-2} + \sum_{m_2} (\hat{\xi}_{m_2} - \xi_{m_2})^2 \times$$
$$\sigma_{m_2}^{-2} + \sum_{m_3} (\hat{\xi}_{m_3} - \xi_{m_3})^2 \times \sigma_{m_3}^{-2} + L^2$$

where $L^2=[(x_1-x_2)(y_1-y_3)-(x_1-x_3)(y_{1-y_2})]^2+[(x_1-x_2)(z_1-z_3)-(x_1-x_3)(z_1-z_2)]^2+[(y_1-y_2)(z_1-z_3)-(y_1-y_3)(z_1-z_2)]^2$.

To use Marquardt's algorithm, the derivatives of the objective function with respect to the estimated parameters are taken and the flow chart and Hessian matrix are utilized.

The rotational radius R is preferably optimized first, because variations in the rotational radius R have been found to have a relatively significant effect on the convergence of the other parameters. By distinction, the projected location of the focal point on the detector Cξ and the focal length F can be estimated accurately regardless of variation in the radius.

Five point sources on an orthogonal cross are designed to solve this problem. With the orthogonal five point source of the preferred embodiment, the value $O^2$ of Equation (5), the $O^2$ value is defined as:

$$O^2 = [(x_1-x_2)\cdot(x_4-x_5) + (y_1-y_2)\cdot(y_4-y_5) + (z_1-z_2)\cdot(z_4-z_5)]^2 \tag{32}$$

The values of $L_1^2$ and $L_2^2$ are as discussed above. The Hessian matrix and its derivatives are readily derived as described above. Estimated results show that all the parameters are accurately converged to the designed values regardless of different initial values. Since the coordinates of the point sources can be accurately determined, the average projection bin width can be estimated by:

$$\text{Bin} = \frac{1}{4} \sum_{i=1}^{4} \frac{\hat{d}_i}{\Delta d_i} \tag{33}$$

where $d_i$, in the unit of cm or mm, is the measured distance between each two point sources, and $\Delta d_i$ in the unit of bin grid is the estimated distance between the two point sources.

Although described with reference to fan-beam collimators, the present invention is equally applicable to cone-beam collimators by expanding the above-referenced discussions to two dimensions.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A nuclear camera system comprising:

at least one radiation detector head for detecting radiation in an examination region, the radiation detection head including a collimator;

a means for moving the detector head relative to the examination region;

an image reconstruction means for reconstructing image data from the detector head into a diagnostic image representation;

an image memory for storing the image representation;

a display means for converting at least selected portions of data in the image memory into a human-readable display;

a calibration phantom removably inserted in the examination region, the phantom including first and second lines of radiation sources, each line including at least three radiation sources and the first and second lines having a preselected, fixed orientation relative to each other;

a means for analyzing the data from the detector head as the detector head is moved relative to the phantom to generate detector head misalignment parameter values;

an electronic correcting means for correcting the image reconstruction means in accordance with the misalignment parameter values.

2. The system as set forth in claim 1 wherein the collimator is one of a fan-beam collimator and a conebeam collimator.

3. A radiographic camera system comprising:

at least one radiation detector assembly for detecting radiation exiting from an examination region along a fan-shaped array of paths;

an image reconstruction processor for reconstructing image data from the detector assembly into a diagnostic image representation;

an image memory for storing the image representation;

a monitor for converting at least selected portions of data in the image memory into a human-readable display;

a calibration phantom including first and second lines of radiation sources, each line including at least three radiation sources and the first and second lines having a preselected, fixed orientation relative to each other, the phantom being removably inserted in the examination region;

a means for analyzing the data from the detector head as the detector head is moved relative to the phantom to generate detector assembly misalignment parameters values;

an electronic correcting means for correcting the image reconstruction means in accordance with the misalignment parameter values.

4. The system as set forth in claim 3 wherein the first and second lines intersect with a preselected angle of orientation.

5. The system as set forth in claim 4 wherein the angle of intersection is orthogonal.

6. The system as set forth in claim 4 wherein the first and second lines share a common radiation source disposed at the intersection of the first and second lines.

7. The system as set forth in claim 3 wherein the reconstruction processor includes a weighting means for weighting data from the detector head with a weighting function, a filter for filtering the weighted data, and a backprojector for backprojecting the filtered, weighted data into the image representation for storage in the image memory and wherein:

the correcting means includes a means for adjusting the backprojecting means.

8. The system as set forth in claim 7 wherein the correcting means further includes a means for adjusting the weighting function means.

9. A method of automatically recalibrating a nuclear camera which includes at least one: radiation detector head for detecting radiation in an examination region, a convergent ray collimator focuses at a focal point attached to the radiation detection head, a means for rotating the detector head around the examination region, and an image reconstruction processor for reconstructing image data from the detector head into the diagnostic image representation, the method comprising:

positioning a phantom in the examination region, which phantom includes first and second lines of radiation sources, each tine including at least three radiation sources and the first and second lines having a preselected, fixed orientation relative to each other;

rotating the detector head around the examination region;

from output data from the detector head generated while rotating around the phantom, generating values indicative of misalignment of the detector head;

electronically adjusting the image reconstruction processor in accordance with the misalignment values.

10. The method as set forth in claim 9 wherein the first and second lines intersect with a preselected angle of orientation.

11. The method as set forth in claim 10 wherein the angle of intersection is orthogonal.

12. The method as set forth in claim 10 wherein the first and second lines share a common radiation source disposed at the intersection of the first and second lines.

13. The method as set forth in claim 9 wherein the reconstruction means (i) weights data from the detector head with a weighting function, (ii) filters the weighted data, and (iii) backprojects the filtered, weighted data into the image representation with a backprojection function and wherein:

the adjusting step includes adjusting the backprojection function.

14. The method as set forth in claim 13 wherein the adjusting step further includes adjusting the weighting function.

15. The method as set forth in claim 9 wherein the misalignment values include an offset of an actual axis of rotation relative to a target axis of rotation, an actual distance between the detector head and the actual axis of rotation, a projected location of the focal point on the detector head, and an actual focal length of the collimator.

16. The method as set forth in claim 15 wherein the step of generating the misalignment values includes a $\chi^2$ minimization process.

17. The method as set forth in claim 15 wherein the step of generating the misalignment values includes varying smoothly between conjugate gradient and steepest descent minimization methods in accordance with Marquardt's algorithm.

18. A phantom for a radiographic diagnostic imaging system in which radiation traverses an examination region along divergent paths, a radiation detection assembly which detects the radiation which has traversed the examination region along the divergent paths and producing electronic data indicative thereof, and a reconstruction processor for reconstructing the electronic data into a diagnostic image representation, the phantom comprising:

first and second lines of radiation sources removably disposed in the examination region, each line including at least three radiation sources and the first and second lines having a preselected, fixed orientation relative to each other.

* * * * *

UNITED STATES PATENT AND TRADEMARK OFFICE
CERTIFICATE OF CORRECTION

PATENT NO.    : 5,481,115
DATED         : January 2, 1996
INVENTOR(S)   : Hsieh et al.

It is certified that error appears in the above-identified patent and that said Letters Patent is hereby corrected as shown below:

Column 1,
Line 10, insert -- The US Government has a paid-up license in this invention and the right in limited circumstances to require the patent owner to license on reasonable terms as provided by the terms of NIH Grant No. R01 HL 399792-05 awarded by the National Institute of Health. --

Signed and Sealed this

Twenty-fourth Day of February, 2004

JON W. DUDAS
*Acting Director of the United States Patent and Trademark Office*